United States Patent [19]

Noltes et al.

[11] 4,243,824
[45] Jan. 6, 1981

[54] ZERO-VALENT RHODIUM CATALYST HYDROGENATION

[75] Inventors: Jan G. Noltes, Huis Ter Heide; Gerard van Koten, Bilthoven, both of Netherlands; Murray S. Cohen, Convent Station, N.J.

[73] Assignee: Borg-Warner Corporation, Chicago, Ill.

[21] Appl. No.: 88,242

[22] Filed: Oct. 25, 1979

Related U.S. Application Data

[60] Division of Ser. No. 10,459, Feb. 8, 1979, which is a continuation-in-part of Ser. No. 827,278, Aug. 24, 1977, Pat. No. 4,152,303.

[51] Int. Cl.³ .......................... C07C 5/08; C07N 5/03
[52] U.S. Cl. ................................. 585/259; 585/262; 585/269; 585/277; 585/266
[58] Field of Search ........................................ 585/259

[56] References Cited

U.S. PATENT DOCUMENTS

| | | | |
|---|---|---|---|
| 3,697,449 | 10/1972 | Drake | 252/474 |
| 3,759,838 | 9/1973 | Dewhirst | 252/429 R |
| 3,954,601 | 5/1976 | Cosyns et al. | 585/259 |
| 4,021,374 | 5/1977 | Petro et al. | 252/474 |
| 4,053,515 | 10/1977 | Drake | 252/466 R X |

FOREIGN PATENT DOCUMENTS 2117439  10/1971  Fed. Rep. of Germany .

OTHER PUBLICATIONS

Popov et al., Chem. Ab. 84:73771w.
Alchudzhan et al., Chem. Ab. 71:12280v.
Alchudzhan et al., Chem. Ab. 72:66452s.
Pittman et al., "Metal Cluster Analysis," Chem. Tech., Mar. 1978, pp. 170-175.

*Primary Examiner*—Veronica O'Keefe
*Attorney, Agent, or Firm*—Joseph Shekleton

[57] ABSTRACT

A process for the preparation of novel zero-valent rhodium catalysts. The catalysts are prepared by the reaction of a hydrocarbyl-lithium compound with a hydrocarbon-soluble complex of a rhodium halide and a ligand. The catalyst may, if desired, be deposited on a support such as alumina or silica. It is effective to catalyze the hydrogenation of organic compounds such as benzene, styrene and the like.

2 Claims, No Drawings

ZERO-VALENT RHODIUM CATALYST HYDROGENATION

This is a division of application Ser. No. 10,459 filed Feb. 8, 1979, which is a continuation-in-part of Ser. No. 827,278 filed Aug. 24, 1977 and now U.S. Pat. No. 4,152,303.

The invention of this application relates to a novel catalyst and its method of preparation. More particularly, it relates, as indicated, to a zero-valent rhodium catalyst; the catalyst is effective to promote the hydrogenation of aromatic, olefinic and acetylenic compounds, as well as other reactions normally susceptible to catalysis.

Ten Hoedt et al., J. Organomet. Chem. 133 (1977) 113-121, show the preparation of certain mixed-organocopper cluster compounds by the ligand substitution reaction of $Ar_4Cu_6Br_2$ with two equivalents of LiC-CR.

Popov et al., C.A. 84: 73771w, suggest that the effectiveness of a rhodium-alumina catalyst in the hydrogenation of benzene is directly proportional to the proportion of rhodium in the catalyst. The temperature of the hydrogenation ranged from 100° C. to 160° C.

Alchudzhan et al., C.A. 71: 12280v, studied the temperature dependence of the rate of benzene hydrogenation on the rhodium-silica catalyst. The activity was studied at 200° C., 160° C., 140° C., 115° C., 90° C. and 70° C. The activity-temperature curve showed a maximum at 110° C. Also, the activity of Group VIII metals was shown to decrease in the series rhodium-ruthenium-platinum-palladium.

Alchudzhan et al., C.A. 72: 66452s, show the catalysis of benzene hydrogenation by a silver rhodium mixture and also by a rhodium gold mixture.

Bryce-Smith et al., Ger. Offen. No. 2,117,439, show the preparation of improved transition metal catalysts by treating a salt of the metal with the adduct of an aromatic compound and an alkali metal or alkaline earth metal (other than magnesium).

The invention of the present application is a process for the preparation of a zero-valent rhodium catalyst comprising reacting a hydrocarbyl lithium compound with a hydrocarbon-soluble rhodium halide complex of the formula $RhX_aL_b$ wherein X is chlorine or bromine, L is an olefinic hydrocarbon ligand, a is 1-3 and b is 1-4, in a hydrocarbon solvent. The invention also includes the zero-valent rhodium catalyst thus prepared and its use in the catalysis of hydrogenation reactions. The process preferably is carried out in a dry, oxygen-free atmosphere. The atmosphere may be, e.g., nitrogen, ethylene or argon.

The hydrocarbyl lithium compound may be represented by RLi, where R is aromatic or aliphatic. Typical aromatic radicals include o-tolyl, m-tolyl, p-tolyl, phenyl, 2,4-xylyl, 1-naphthyl, 2-naphthyl, etc. Typical aliphatic radicals include methyl, ethyl, n-propyl, isopropyl, n-butyl, sec-butyl, tert-butyl, n-pentyl, n-hexyl, 3-hexyl, 2-methyl-4-pentyl, etc. Aromatic hydrocarbyl radicals preferably have 6-12 carbon atoms; aliphatic hydrocarbyl radicals preferably have 1-6 carbon atoms.

The hydrocarbyl lithium compounds may be prepared by the reaction of lithium metal with the appropriate aliphatic or aromatic chlorine or bromine substituted hydrocarbon. Thus, the reaction of lithium with bromobenzene yields phenyl lithium.

The rhodium halide complex has the composition indicated by the formula $RhX_aL_b$. The halide may be chlorine or bromine. Chlorine is preferred. The olefinic hydrocarbon ligand (L) is construed broadly; specific illustrative embodiments include ethylene, cyclooctadiene-1,3, norbornadiene, butadiene, isoprene, 1-hexene, and the like. Olefinic hydrocarbons having up to 12 carbon atoms are contemplated. Examples of rhodium halide complexes include $RhCl(CH_2=CH_2)_2$, RhBr.cyclooctadiene, RhCl.norbornadiene, etc. A method for preparing the rhodium chloride ethylene complex is shown by R. Cramer, J. Am. Chem. Soc., 86: (1964) 217.

The process is carried out very simply, merely by mixing the reactants at room temperature, i.e., from about 20° C. to about 30° C. The temperature is not a critical feature of the process and lower or higher temperatures may be used depending, for the most part, on the particular reactants which are used. A reaction occurs at once. The zero-valent rhodium product may be used as such in a catalytic hydrogenation, or it may be deposited on a support and isolated by decanting the hydrocarbon solvent away from the solid product. The support may be any of those commonly used in catalytic chemistry, viz., alumina, silica, clay and the like.

The process is carried out in a solvent. The reactants may not be completely soluble in the solvent, and the zero-valent metal product is not soluble so that agitation of the process mixture is highly desirable. Suitable solvents include benzene, toluene, xylene, ethylbenzene, pentane, cyclohexane and, in fact, any hydrocarbon solvent which is normally liquid, i.e., liquid at about room temperature.

Relative proportions of the rhodium halide complex and the hydrocarbyl-lithium are indicated by the stoichiometry of the reaction. Care should be taken not to use an excess of the hydrocarbyl-lithium compound in which case the resulting product shows no catalytic activity. At the same time, however, addition of a small amount of water to such a product is effective to convert it to an efficient catalyst.

The hydrogenation reactions which are catalyzed by the zero-valent metal products herein may in most instances be carried out at room temperature and at ordinary pressures. Aromatic compounds, i.e., the aromatic ring, can be hydrogenated merely by introducing hydrogen into a reaction vessel containing the aromatic compound and the catalyst. Benzene and naphthalene, for example, can be hydrogenated in this fashion, benzene yielding cyclohexane and naphthalene yielding a mixture of cis- and trans-decalin. Olefinic compounds can also be hydrogenated under similar conditions. Styrene, for example, can be converted to ethylbenzene and then to ethylcyclohexane. Stilbene can be converted to 1,2-diphenylethane and then to 1,2-dicyclohexylethane. Phenylacetylene can be hydrogenated likewise to ethylbenzene, and then to ethylcyclohexane.

The activity of the hydrogenation catalyst varies with its concentration in the hydrogenation mixture. In benzene, for example, the activity, measured in ml. of hydrogen absorbed per minute per mmol of zero-valent rhodium, increases as the catalyst concentration decreases from 0.067 mmol of Rh/ml. (of benzene) to 0.008 mmol of Rh/ml., then decreases upon further decrease of catalyst cencentration.

In Example 5 of the above-identified Application Ser. No. 827,278, filed Aug. 24, 1977, now U.S. Pat. No. 4,152,303 there is described the preparation of a zero-valent gold-rhodium product, as follows: To a suspension of 0.5 mmol of p-tolylgoldlithium etherate (p-tol)$_4$Au$_2$Li$_2$(C$_2$H$_5$OC$_2$H$_5$)$_2$ in 30 ml. of benzene under nitrogen, there is added with stirring 1.0 mmol of rhodium chloride ethylene complex (RhCl.(CH$_2$=CH$_2$)$_2$). Immediately, the color of the suspension darkens, indicating the formation of (p-tol)$_4$Au$_2$Rh$_2$, followed immediately by its decomposition to the desired Au°/Rh°.

EXAMPLE 1

The preparation of Rh° may be accomplished in a similar manner, reacting p-tolLi with a rhodium halide complex such as the ethylene complex. An unstable intermediate similar to the above polymetal structure is formed and then the desired Rh° metal.

EXAMPLE 2

A rhodium chloride-cyclooctadiene complex is prepared by the method of J. Chatt et al., J. Chem. Soc., (1957) 4735. To a solution of 10 g. of rhodium trichloride hydrate.(RhCl$_3$.3H$_2$O) in 300 ml. of ethanol there is added 21 ml. of cyclooctadiene and the resulting mixture heated at reflux temperature for three hours. The cooled mixture is filtered yielding the solid rhodium chloride-cyclooctadiene complex, (RhCl.COD)$_2$, M.P. 249°–250° C.

EXAMPLE 3

A solution of 30.67 mg. (0.125 mmol) of rhodium chloride.cyclooctadiene complex in 15 ml. of benzene, under nitrogen, is treated at room temperature with 0.008 mg. (0.125 mmol) of n-butyl lithium. Immediately, the mixture is flushed with hydrogen. A slightly exothermic reaction ensues and the right yellow solution is converted to a dark brown slurry.

The catalytic activity of the above resulting zero-valent rhodium product slurry is determined by attaching to the reaction flask, through a stopcock, a gas burnt filled with hydrogen and equipped with a leveling bulb. The nitrogen is evacuated and the flask filled with hydrogen to atmospheric pressure (744 mm. ) and the contents of the flask shaken vigorously. The hydrogenation of the benzene is monitored by observing the decrease of gas volume in the buret. The rate of hydrogenation is found to be 1120 ml./min./mmol of zero-valent rhodium.

Naphthalene, stilbene, styrene, phenylacetylene and other aromatic, olefinic and acetylenic compounds may be hydrogenated similarly.

All parts and percentages herein are by weight unless otherwise expressly stated.

We claim:

1. A process for the hydrogenation of aromatic, olefinic and acetylenic compounds comprising treating such compounds with hydrogen in the presence of a zero-valent rhodium catalyst prepared by a process comprising reacting a hydrocarbyllithium compound with a rhodium halide complex of the formula Rh X$_a$L$_b$ where X is a chlorine or bromine, L is an olefinic hydrocarbon ligand, a is 1–3 and b is 1–4 in a hydrobcarbon solvent.

2. The process of claim 1, wherein the hydrogenation is carried out at about room temperature.

* * * * *